(12) United States Patent
Jeong et al.

(10) Patent No.: US 11,219,667 B2
(45) Date of Patent: Jan. 11, 2022

(54) METHOD FOR TREATING PERIPHERAL VASCULAR DISEASE USING HEPATOCYTE GROWTH FACTOR AND STROMAL CELL DERIVED FACTOR 1A

(71) Applicant: Helixmith Co., Ltd., Seoul (KR)

(72) Inventors: Jae-Gyun Jeong, Seoul (KR); Jung Hun Lee, Seoul (KR); Nayeon Lee, Seoul (KR)

(73) Assignee: Helixmith Co., Ltd., Seoul (KR)

( * ) Notice: Subject to any disclaimer, the term of this patent is extended or adjusted under 35 U.S.C. 154(b) by 0 days.

(21) Appl. No.: 15/514,244

(22) PCT Filed: Sep. 25, 2015

(86) PCT No.: PCT/KR2015/010240
§ 371 (c)(1),
(2) Date: May 16, 2018

(87) PCT Pub. No.: WO2016/048105
PCT Pub. Date: Mar. 31, 2016

(65) Prior Publication Data
US 2017/0281729 A1    Oct. 5, 2017

(51) Int. Cl.
*A61K 48/00* (2006.01)
*A61K 38/19* (2006.01)
*A61K 38/18* (2006.01)

(52) U.S. Cl.
CPC ............ *A61K 38/195* (2013.01); *A61K 38/18* (2013.01); *A61K 38/1833* (2013.01); *A61K 48/00* (2013.01); *A61K 48/0016* (2013.01)

(58) Field of Classification Search
None
See application file for complete search history.

(56) References Cited

U.S. PATENT DOCUMENTS

| | | |
|---|---|---|
| 5,994,109 A | 11/1999 | Woo et al. |
| 7,473,425 B2 | 1/2009 | Fukuda et al. |
| 8,435,953 B2 | 5/2013 | Tabata |
| 2005/0079581 A1 | 4/2005 | Kim et al. |
| 2013/0095060 A1 | 4/2013 | Hsieh et al. |

FOREIGN PATENT DOCUMENTS

| | | |
|---|---|---|
| CN | 1466463 A | 1/2004 |
| CN | 1643149 A | 7/2005 |
| CN | 1894280 A | 1/2007 |
| CN | 101437576 A | 5/2009 |
| CN | 101796188 A | 8/2010 |
| CN | 101925362 A | 12/2010 |
| WO | WO-00/040737 A1 | 7/2000 |
| WO | WO-03/078568 A2 | 9/2003 |
| WO | WO-2007/095353 A2 | 8/2007 |
| WO | WO-2008/121719 A1 | 10/2008 |
| WO | WO 2010/138180 | * 12/2010 |
| WO | WO-2012/025925 A1 | 3/2012 |
| WO | WO-2012/027170 A1 | 3/2012 |
| WO | WO-2012/170495 A1 | 12/2012 |

OTHER PUBLICATIONS

Niidome et al. (Gene Ther. 9:1647-1652; 2002), (Year: 2002).*
Bouard et al. (Br J Pharmacol, 157(2):153-65, 2009) (Year: 2009).*
Ouma et al (Vase Med, 17(3): 1-28, 2012) (Year: 2012).*
Extended European Search Report dated Mar. 29, 2018 for European Patent Application No. 15843739.2, Jeong et al., "Composition for Preventing or Treating Peripheral Vascular Disease Using Hepatocyte Growth Factor and Stromal Cell Derived Factor 1-alpha," filed Sep. 25, 2015 (11 pages).
Majka et al., "SDF-1 alone and in co-operation with HGF regulates biology of human cervical carcinoma cells," Folia Histochemica et Cytobiologica. 44(3):155-64 (2006).
Murohara, "Autologous adipose tissue as a new source of progenitor cells for therapeutic angiogenesis," J Cardiol. 53(2):155-63 (2009).
Deveza, Lorenzo, Dissertation: "Harnessing stem cells as drug delivery vehicles for therapeutic angiogensis: a biomaterials-mediated approach," Doctor of Philosophy in Bioengineering, Stanford University, 2014 (171 pages).
Hiasa et al., "Gene transfer of stromal cell-derived factor-1 alpha enhances ischemic vasculogenesis and angiogenesis via vascular endothelial growth factor/endothelial nitric oxide synthase-related pathway: next-generation chemokine therapy for therapeutic neovascularization," Circulation. 109(20):2454-61 (2004) (9 pages).
Ho et al., "Stromal-cell-derived factor-1 (SDF-1)/CXCL12 as potential target of therapeutic angiogenesis in critical leg ischaemia," Cardiol Res Pract. 2012:143209 (2012) (8 pages).
Kuliszewski et al., "Vascular gene transfer of SDF-1 promotes endothelial progenitor cell engraftment and enhances angiogenesis in ischemic muscle," Mol Ther. 19(5):895-902 (2011).

(Continued)

*Primary Examiner* — Anoop K Singh
*Assistant Examiner* — Magdalene K Sgagias
(74) *Attorney, Agent, or Firm* — Clark & Elbing LLP; Susan M. Michaud

(57) ABSTRACT

The present invention relates to a pharmaceutical composition for preventing or treating peripheral vascular disease, the composition comprising, as an active ingredient: (a) hepatocyte growth factor (HGF) or an isoform thereof, and stromal cell derived factor 1α (SDF-1α); or (b) a polynucleotide encoding the HGF and a polynucleotide encoding the SDF-1α. The peripheral vascular disease (for example, ischemic limb disease) can be more effectively prevented or treated through the significant promotion of vascular endothelial cell migration and angiogenesis in the case of singly using the composition of the present invention than in the case of using HGF, an isoform thereof, SDF-1α or a polynucleotide codes a protein thereof.

9 Claims, 3 Drawing Sheets
Specification includes a Sequence Listing.

(56) References Cited

OTHER PUBLICATIONS

Makino et al., "Progress and prospects of therapeutic angiogenesis using HGF plasmid gene therapy for peripheral arterial disease," Journal of Japanese College of Angiology. 47:187-93 (2007) (English abstract provided) (8 pages).

Morishita et al., "Phase I/IIa clinical trial of therapeutic angiogenesis using hepatocyte growth factor gene transfer to treat critical limb ischemia," Arterioscler Thromb Vasc Biol. 31 (3):713-20 (2011) (14 pages).

Office Action dated Dec. 26, 2017 for Japanese Patent Application No. 2017-516357, Jeong et al., "Composition for preventing or treating peripheral vascular disease using hepatocyte growth factor and stromal cell derived factor 1 A," filed Sep. 25, 2015 (11 pages).

Rosova et al., "Hypoxic preconditioning results in increased motility and improved therapeutic potential of human mesenchymal stem cells," Stem Cells. 26(8):2173-82 (2008).

Segers et al., "Protease-resistant stromal cell-derived factor-1 for the treatment of experimental peripheral artery disease," Circulation. 123(12):1306-15 (2011) (20 pages).

Son et al., "Migration of bone marrow and cord blood mesenchymal stem cells in vitro is regulated by stromal-derived factor-1-CXCR4 and hepatocyte growth factor-c-met axes and involves matrix metalloproteinases," Stem Cells. 24(5):1254-64 (2006).

Yamaguchi et al., "Stromal cell-derived factor-1 effects on ex vivo expanded endothelial progenitor cell recruitment for ischemic neovascularization," Circulation. 107(9):1322-8 (2003) (8 pages).

Yu et al., "Combination of stromal-derived factor-1 alpha and vascular endothelial growth factor gene-modified endothelial progenitor cells is more effective for ischemic neovascularization," J Vasc Surg. 50(3):608-16 (2009).

Clayton et al., "Vascular Endothelial Growth Factor-A Specifies Formation of Native Collaterals and Regulates Collateral Growth in Ischemia," available in PMC Oct. 24, 2009, published in final edited form as: Circ Res. 103(9):1027-36 (2008) (17 pages).

Couffinhal et al., "Mouse model of angiogenesis," Am J Pathol. 152(6):1667-79 (1998).

International Search Report for International Application No. PCT/KR2015/010240, dated Jan. 20, 2016, Jeong et al., "Composition for Preventing or Treating Peripheral Vascular Disease Using Hepatocyte Growth Factor and Stromal Cell Derived Factor 1 A," filed Sep. 25, 2015 (8 pages).

Limbourg et al., "Evaluation of postnatal arteriogenesis and angiogenesis in a mouse model of hind-limb ischemia," Nat Protoc. 4(12):1737-48 (2009).

Sanada et al., "Therapeutic angiogenesis by gene therapy for critical limb ischemia: choice of biological agent," Immun. Endoc. Metab. Agents Med. Chem. 14(1):32-39 (2014).

First Office Action dated May 18, 2020 for Chinese Patent Application No. 201580051957.1, Jeong et al., "Composition for Preventing or Treating Peripheral Vascular Disease Using Hepatocyte Growth Factor and Stromal Cell Derived Factor 1A," filed Sep. 25, 2015 (20 pages).

\* cited by examiner

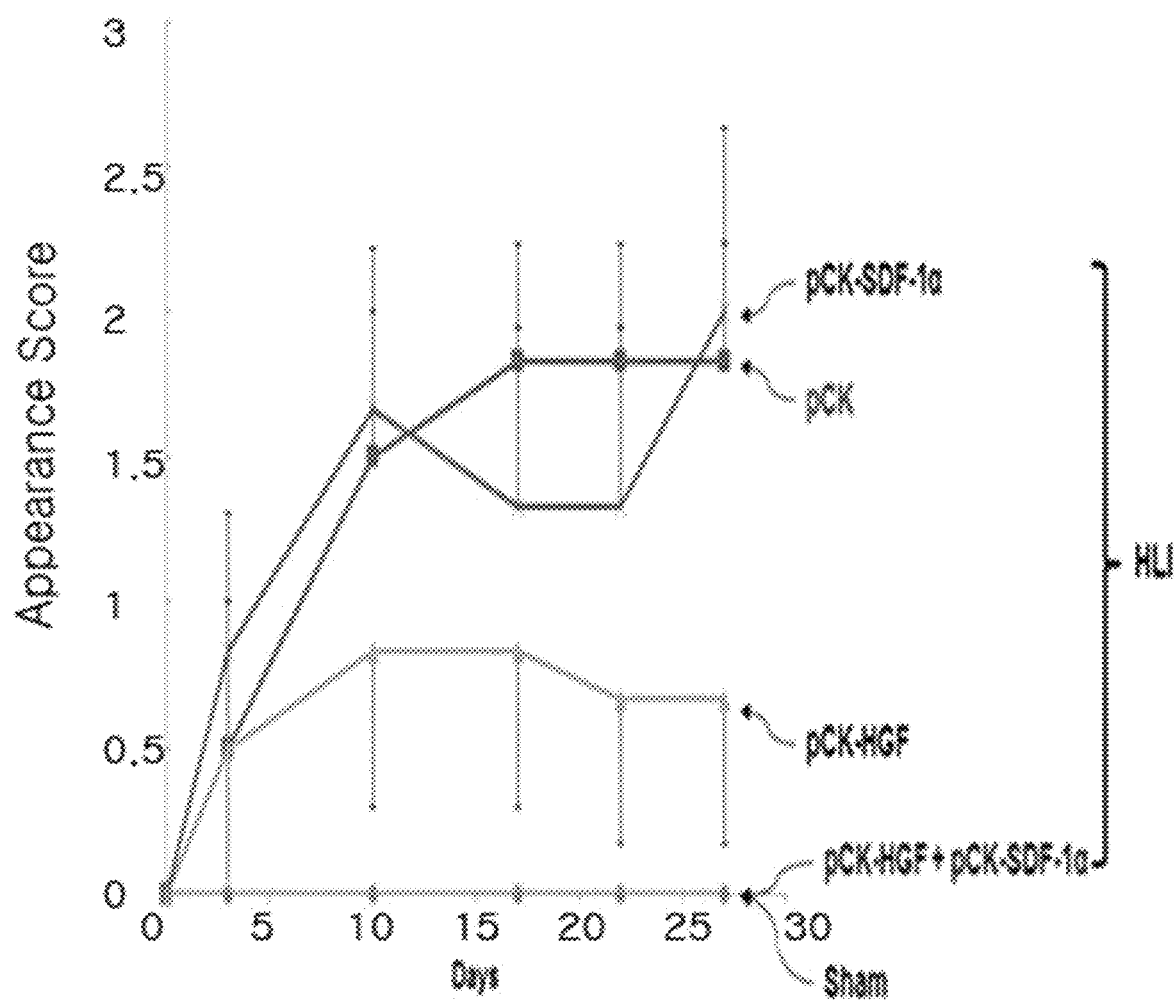

SEQUENCE LISTING

```
<160> NUMBER OF SEQ ID NOS: 11

<210> SEQ ID NO 1
<211> LENGTH: 697
<212> TYPE: PRT
<213> ORGANISM: Homo sapiens

<400> SEQUENCE: 1

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
```

```
            20                  25                  30
Val Asn Thr Ala Asp Gln Cys Ala Asn Arg Cys Thr Arg Asn Lys Gly
             35                  40                  45
Leu Pro Phe Thr Cys Lys Ala Phe Val Phe Asp Lys Ala Arg Lys Gln
             50                  55                  60
Cys Leu Trp Phe Pro Phe Asn Ser Met Ser Ser Gly Val Lys Lys Glu
 65                  70                  75                  80
Phe Gly His Glu Phe Asp Leu Tyr Glu Asn Lys Asp Tyr Ile Arg Asn
                 85                  90                  95
Cys Ile Ile Gly Lys Gly Arg Ser Tyr Lys Gly Thr Val Ser Ile Thr
                100                 105                 110
Lys Ser Gly Ile Lys Cys Gln Pro Trp Ser Ser Met Ile Pro His Glu
            115                 120                 125
His Ser Phe Leu Pro Ser Ser Tyr Arg Gly Lys Asp Leu Gln Glu Asn
            130                 135                 140
Tyr Cys Arg Asn Pro Arg Gly Glu Glu Gly Gly Pro Trp Cys Phe Thr
145                 150                 155                 160
Ser Asn Pro Glu Val Arg Tyr Glu Val Cys Asp Ile Pro Gln Cys Ser
                165                 170                 175
Glu Val Glu Cys Met Thr Cys Asn Gly Glu Ser Tyr Arg Gly Leu Met
                180                 185                 190
Asp His Thr Glu Ser Gly Lys Ile Cys Gln Arg Trp Asp His Gln Thr
            195                 200                 205
Pro His Arg His Lys Phe Leu Pro Glu Arg Tyr Pro Asp Lys Gly Phe
            210                 215                 220
Asp Asp Asn Tyr Cys Arg Asn Pro Asp Gly Gln Pro Arg Pro Trp Cys
225                 230                 235                 240
Tyr Thr Leu Asp Pro His Thr Arg Trp Glu Tyr Cys Ala Ile Lys Thr
                245                 250                 255
Cys Ala Asp Asn Thr Met Asn Asp Thr Asp Val Pro Leu Glu Thr Thr
                260                 265                 270
Glu Cys Ile Gln Gly Gln Gly Glu Gly Tyr Arg Gly Thr Val Asn Thr
            275                 280                 285
Ile Trp Asn Gly Ile Pro Cys Gln Arg Trp Asp Ser Gln Tyr Pro His
            290                 295                 300
Glu His Asp Met Thr Pro Glu Asn Phe Lys Cys Lys Asp Leu Arg Glu
305                 310                 315                 320
Asn Tyr Cys Arg Asn Pro Asp Gly Ser Glu Ser Pro Trp Cys Phe Thr
                325                 330                 335
Thr Asp Pro Asn Ile Arg Val Gly Tyr Cys Ser Gln Ile Pro Asn Cys
            340                 345                 350
Asp Met Ser His Gly Gln Asp Cys Tyr Arg Gly Asn Gly Lys Asn Tyr
            355                 360                 365
Met Gly Asn Leu Ser Gln Thr Arg Ser Gly Leu Thr Cys Ser Met Trp
            370                 375                 380
Asp Lys Asn Met Glu Asp Leu His Arg His Ile Phe Trp Glu Pro Asp
385                 390                 395                 400
Ala Ser Lys Leu Asn Glu Asn Tyr Cys Arg Asn Pro Asp Asp Asp Ala
                405                 410                 415
His Gly Pro Trp Cys Tyr Thr Gly Asn Pro Leu Ile Pro Trp Asp Tyr
            420                 425                 430
Cys Pro Ile Ser Arg Cys Glu Gly Asp Thr Thr Pro Thr Ile Val Asn
            435                 440                 445
```

Leu Asp His Pro Val Ile Ser Cys Ala Lys Thr Lys Gln Leu Arg Val
         450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
                 485                 490                 495

Trp Val Leu Thr Ala Arg Gln Cys Phe Pro Ser Arg Asp Leu Lys Asp
             500                 505                 510

Tyr Glu Ala Trp Leu Gly Ile His Asp Val His Gly Arg Gly Asp Glu
         515                 520                 525

Lys Cys Lys Gln Val Leu Asn Val Ser Gln Leu Val Tyr Gly Pro Glu
         530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                 565                 570                 575

Glu Lys Thr Ser Cys Ser Val Tyr Gly Trp Gly Tyr Thr Gly Leu Ile
             580                 585                 590

Asn Tyr Asp Gly Leu Leu Arg Val Ala His Leu Tyr Ile Met Gly Asn
         595                 600                 605

Glu Lys Cys Ser Gln His His Arg Gly Lys Val Thr Leu Asn Glu Ser
         610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                 645                 650                 655

Leu Gly Val Ile Val Pro Gly Arg Gly Cys Ala Ile Pro Asn Arg Pro
             660                 665                 670

Gly Ile Phe Val Arg Val Ala Tyr Tyr Ala Lys Trp Ile His Lys Ile
         675                 680                 685

Ile Leu Thr Tyr Lys Val Pro Gln Ser
         690                 695

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
             20                  25                  30

Arg Lys Arg Arg Asn Thr Ile His Glu Phe Lys Lys Ser Ala Lys Thr
         35                  40                  45

Thr Leu Ile Lys Ile Asp Pro Ala Leu Lys Ile Lys Thr Lys Lys Val
     50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
             100                 105                 110

Gly His Glu Phe Asp Leu Tyr Glu Asn Lys Asp Tyr Ile Arg Asn Cys

```
            115                 120                 125
Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540
```

```
Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 3
<211> LENGTH: 723
<212> TYPE: PRT
<213> ORGANISM: Artificial Sequence
<220> FEATURE:
<223> OTHER INFORMATION: Synthetic Construct

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175
```

-continued

```
Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
        435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590
```

```
Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 4
<211> LENGTH: 68
<212> TYPE: PRT
<213> ORGANISM: Homo sapiens

<400> SEQUENCE: 4

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 5
<211> LENGTH: 3679
<212> TYPE: DNA
<213> ORGANISM: Artificial Sequence
<220> FEATURE:
<223> OTHER INFORMATION: Synthetic Construct

<400> SEQUENCE: 5
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa atcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc ttttttacat gttaacagtc     540
tcatattagt ccttcagaat aattctacaa tcctaaaata acttagccaa cttgctgaat     600
```

```
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tcctgggtag gaaacacatt tgaatggtat ttactaagat actaaaatcc    780
ttggacttca ctctaatttt agtgccattt agaactcaag gtctcagtaa aagtagaaat    840
aaagcctgtt aacaaaacac aagctgaata ttaaaaatgt aactggattt tcaaagaaat    900
gtttactggt attacctgta gatgtatatt ctttattatg atcttttgtg taaagtctgg    960
cagacaaatg caatatctaa ttgttgagtc caatatcaca agcagtacaa aagtataaaa   1020
aagacttggc cttttctaat gtgttaaaat actttatgct ggtaataaca ctaagagtag   1080
ggcactagaa attttaagtg aagataatgt gttgcagtta ctgcactcaa tggcttacta   1140
ttataaacca aaactgggat cactaagctc cagtcagtca aaatgatcaa aattattgaa   1200
gagaataagc aattctgttc tttattagga cacagtagat acagactaca aagtggagtg   1260
tgcttaataa gaggtagcat ttgttaagtg tcaattactc tattatccct tggagcttct   1320
caaaataacc atataaggtg taagatgtta aaggttatgg ttacactcag tgcacaggta   1380
agctaatagg ctgagagaag ctaaattact tactggggtc tcacagtaag aaagtgagct   1440
gaagtttcag cccagattta actggattct gggctcttta ttcatgttac ttcatgaatc   1500
tgtttctcaa ttgtgcagaa aaaggggggc tatttataag aaaagcaata aacaaacaag   1560
taatgatctc aaataagtaa tgcaagaaat agtgagattt caaaatcagt ggcagcgatt   1620
tctcagttct gtcctaagtg gccttgctca atcacctgct atctttttagt ggagctttga   1680 aattatgttt cagacaactt cgattcagtt ctagaatgtt tgactcagca aattcacagg   1740
ctcatctttc taacttgatg gtgaatatgg aaattcagct aaatggatgt taataaaatt   1800
caaacgtttt aaggacagat gaaaatgaca gaattttaag gtaaaatata tgaaggaata   1860
taagataaag gattttctca ccttcagcaa aaacataccc actaattagt aaaattaata   1920
ggcaaaaaaa agttgcatgc tcttatactg taatgattat cattttaaaa ctagcttttt   1980
gccttcgagc tatcggggta aagacctaca ggaaaactac tgtcgaaatc ctcgagggga   2040 agaagggga ccctggtgtt tcacaagcaa tccagaggta cgctacgaag tctgtgacat   2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt ggaaacaac    2400 tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc caaacatccg agttggctac tgctcccaaa ttccaaactg   2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta aatgggattc caacacgaac   3000
```

```
aaacatagga tggatggtta gtttgagata cagaaataaa catatctgcg gaggatcatt    3060
gataaaggag agttgggttc ttactgcacg acagtgtttc ccttctcgag acttgaaaga    3120
ttatgaagct tggcttggaa ttcatgatgt ccacggaaga ggagatgaga aatgcaaaca    3180
ggttctcaat gtttcccagc tggtatatgg ccctgaagga tcagatctgg ttttaatgaa    3240
gcttgccagg cctgctgtcc tggatgattt tgttagtacg attgatttac ctaattatgg    3300
atgcacaatt cctgaaaaga ccagttgcag tgtttatggc tggggctaca ctggattgat    3360
caactatgat ggcctattac gagtggcaca tctctatata tgggaaatg agaaatgcag     3420 ccagcatcat cgagggaagg tgactctgaa tgagtctgaa atatgtgctg gggctgaaaa    3480
gattggatca ggaccatgtg aggggatta tggtggccca cttgtttgtg agcaacataa     3540
aatgagaatg gttcttggtg tcattgttcc tggtcgtgga tgtgccattc caaatcgtcc    3600
tggtattttt gtccgagtag catattatgc aaaatggata cacaaaatta ttttaacata    3660
taaggtacca cagtcatag                                                3679

<210> SEQ ID NO 6
<211> LENGTH: 270
<212> TYPE: DNA
<213> ORGANISM: Homo sapiens

<400> SEQUENCE: 6
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga gaacaacaa cagacaagtg tgcattgacc cgaagctaaa gtggattcag      240
gagtacctgg agaaagcttt aaacaagtaa                                     270

<210> SEQ ID NO 7
<211> LENGTH: 7113
<212> TYPE: DNA
<213> ORGANISM: Artificial Sequence
<220> FEATURE:
<223> OTHER INFORMATION: Synthetic Construct

<400> SEQUENCE: 7
atgtgggtga ccaaactcct gccagccctg ctgctgcagc atgtcctcct gcatctcctc      60
ctgctcccca tcgccatccc ctatgcagag ggacaaagga aagaagaaa tacaattcat      120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa acaatgcct ctggttcccc      300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc tttttacat gttaacagtc     540 tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaattg tagatctcgg      720 tatttgtgaa ataataacgt aaacttcgtt taaaaggatt cttcttcctg tctttgagaa    780
```

```
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt attttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagtttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccattttggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaaacaac aattttcaaa attagttact   1860
tacaattatg tagaaatgcc tctaaaacac agtattttcc ttatattaca aaaacaaaaa   1920
ttataattgg ttttgtcctc ttttgagagt ttgcatggtg ttactccctg catagtgaag   1980
aaaacatttt atttaagtag atggatctaa gttttcatg aacaaaggaa tgacatttga   2040
aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct ctttttaccaa tgaacacttc cttgtgatat   2220
agatgtttat ggccgagagg atccagtata ttaataaaat cccttttttgt attcaatgag   2280 ggaaacacat aattttcatc aattagcagc ttattggaat atctgcatga tggtttaaca   2340
cttttaagtg ttgactaaag attaatttta cagaaaatag aaaaagaaat atgtttctgt   2400
ctggaggaat gatttattgt tgaccccta attgaaatat tttactagtg cttaatgga    2460 aagatgatga aagatgatga aattaatgta gaagcttaac tagaaaatca ggtgacctga   2520
tatctacatc tgtatccttc attggccacc cagcattcat taatgaatca gatgatggaa   2580
tagatcaagt ttcctaggaa cacagtgaat attaaaagaa aacaaaggga gcctagcacc   2640
tagaagacct agtttatatt tcaaagtata tttggatgta acccaatttt aaacatttcc   2700
tcacttgtct ctcttaaagc cttgccaaca gcaaggacag agaaccaaaa atagtgtata   2760
tatgaataaa tgcttattac agaatctgct gactggcaca tgctttgtgt gtaatgggtt   2820
ctcataaaca cttgttgaat gaacacacat aagtgaaaga gcatggctag gcttcatccc   2880
ttggtcaaat atggggtgct aaagaaaagc agggaaata cattgggaca ctaacaaaaa   2940
aaaacagtta atttaggtaa aagataaaat acaccacaga atgaagaaaa gagatgaccc   3000
agactgctct ttaaccttca tgtcctagag aggtttttga tatgaattgc attcagaatt   3060
gtggaaagga gcccatcttt tctcttcatt ttgattttat taactccaat ggggaattt    3120 tattcgtgtt ttggccatat ctactttga tttctacatt attctctctt cctttctacc   3180
```

```
tgtatttgtc ctaataaatt gttgacttat taattcacta cttcctcaca gcttttttt       3240 ggctttacaa atccactgga aaggtatatg ggtgtatcac tttgtgtatt tcggtgtgca      3300
tgtgtagagg ggacaaaaat cctctctcaa actataaata ttgagtattt gtgtattgaa      3360
catttgctat aactactagg tttcttaaat aatcttaata tataaaatga tatagaaaaa      3420
gggaaattat agttcgtatt attcatctaa gtgaagagat taaaacccag ggagtaaata      3480
aattgtctaa ggactaaggt tgtatactat ttaggtgata gatatggggc aaccgtatgg      3540
gttttatgat taacaaataa acttctcacc actctaccat atcaactttt ccataaaaga      3600
gagctatagt attctttgct taaataaatt tgattagtgc atgacttctt gaaaacatat      3660
aaagcaaaag tcacatttga ttctatcaga aaagtgagta agccatggcc caaacaaaag      3720
atgcattaaa atattctgga atgatggagc taaaagtaag aaaaatgact ttttaaaaaa      3780
gtttactgtt aggaattgtg aaattatgct gaattttagt tgcattataa ttttttgtcag     3840 tcatacggtc tgacaacctg tcttatttct atttccccat atgaggaatg ctagttaagt     3900
atggatatta actattacta cttagatgca ttgaagttgc ataatatgga taatacttca     3960
ctggttccct gaaaatgttt agttagtaat aagtctctta cactatttgt tttgtccaat     4020
aatttatatt ttctgaagac ttaactctag aatacactca tgtcaaaatg aaagaatttc     4080
attgcaaaat attgcttggt acatgacgca tacctgtatt tgttttgtgt cacaacatga     4140
aaaatgatgg tttattagaa gtttcattgg gtaggaaaca catttgaatg gtatttacta     4200
agatactaaa atccttggac ttcactctaa ttttagtgcc atttagaact caaggtctca     4260
gtaaaagtag aaataaagcc tgttaacaaa acacaagctg aatattaaaa atgtaactgg     4320
attttcaaag aaatgtttac tggtattacc tgtagatgta tattctttat tatgatcttt     4380
tgtgtaaagt ctggcagaca aatgcaatat ctaattgttg agtccaatat cacaagcagt     4440
acaaaagtat aaaaaagact tggccttttc taatgtgtta aaatacttta tgctggtaat     4500
aacactaaga gtagggcact agaaatttta agtgaagata atgtgttgca gttactgcac     4560
tcaatggctt actattataa accaaaactg ggatcactaa gctccagtca gtcaaaatga     4620
tcaaaattat tgaagagaat aagcaattct gttctttatt aggacacagt agatacagac     4680
tacaaagtgg agtgtgctta ataagaggta gcatttgtta agtgtcaatt actctattat     4740
cccttggagc ttctcaaaat aaccatataa ggtgtaagat gttaaaggtt atggttacac     4800
tcagtgcaca ggtaagctaa taggctgaga gaagctaaat tacttactgg ggtctcacag     4860
taagaaagtg agctgaagtt tcagcccaga tttaactgga ttctgggctc tttattcatg     4920
ttacttcatg aatctgtttc tcaattgtgc agaaaaaagg gggctattta agaaaagc      4980 aataaacaaa caagtaatga tctcaaataa gtaatgcaag aaatagtgag atttcaaaat     5040
cagtggcagc gatttctcag ttctgtccta agtggccttg ctcaatcacc tgctatcttt     5100
tagtggagct ttgaaattat gtttcagaca acttcgattc agttctagaa tgtttgactc     5160
agcaaattca caggctcatc tttctaactt gatggtgaat atggaaattc agctaaatgg     5220
atgttaataa aattcaaacg ttttaaggac agatgaaaat gacagaattt taaggtaaaa     5280
tatatgaagg aatataagat aaaggatttt tctaccttca gcaaaaacat acccactaat     5340
tagtaaaatt aataggcaaa aaaagttgc atgctcttat actgtaatga ttatcatttt      5400
aaaactagct ttttgccttc gagctatcgg ggtaaagacc tacaggaaaa ctactgtcga     5460
aatcctcgag gggaagaagg gggaccctgg tgtttcacaa gcaatccaga ggtacgctac     5520
```

| | | | | |
|---|---|---|---|---|
| gaagtctgtg | acattcctca | gtgttcagaa | gttgaatgca | tgacctgcaa tggggagagt | 5580 |
| tatcgaggtc | tcatggatca | tacagaatca | ggcaagattt | gtcagcgctg ggatcatcag | 5640 |
| acaccacacc | ggcacaaatt | cttgcctgaa | agatatcccg | acaagggctt tgatgataat | 5700 |
| tattgccgca | atcccgatgg | ccagccgagg | ccatggtgct | atactcttga ccctcacacc | 5760 |
| cgctgggagt | actgtgcaat | aaaacatgc | gctgacaata | ctatgaatga cactgatgtt | 5820 |
| cctttggaaa | caactgaatg | catccaaggt | caaggagaag | gctacagggg cactgtcaat | 5880 |
| accatttgga | atggaattcc | atgtcagcgt | tgggattctc | agtatcctca cgagcatgac | 5940 |
| atgactcctg | aaaatttcaa | gtgcaaggac | ctacgagaaa | attactgccg aaatccagat | 6000 |
| gggtctgaat | caccctggtg | ttttaccact | gatccaaaca | tccgagttgg ctactgctcc | 6060 |
| caaattccaa | actgtgatat | gtcacatgga | caagattgtt | atcgtgggaa tgcaaaaat | 6120 |
| tatatgggca | acttatccca | aacaagatct | ggactaacat | gttcaatgtg ggacaagaac | 6180 |
| atggaagact | acatcgtca | tatcttctgg | gaaccagatg | caagtaagct gaatgagaat | 6240 |
| tactgccgaa | atccagatga | tgatgctcat | ggaccctggt | gctacacggg aaatccactc | 6300 |
| attccttggg | attattgccc | tatttctcgt | tgtgaaggtg | ataccacacc tacaatagtc | 6360 |
| aatttagacc | atcccgtaat | atcttgtgcc | aaaacgaaac | aattgcgagt tgtaaatggg | 6420 |
| attccaacac | gaacaaacat | aggatggatg | gttagtttga | gatacagaaa taaacatatc | 6480 |
| tgcggaggat | cattgataaa | ggagagttgg | gttcttactg | cacgacagtg tttccccttct | 6540 |
| cgagacttga | agattatga | agcttggctt | ggaattcatg | atgtccacgg aagaggagat | 6600 |
| gagaaatgca | aacaggttct | caatgtttcc | cagctggtat | atggccctga aggatcagat | 6660 |
| ctggttttaa | tgaagcttgc | caggcctgct | gtcctggatg | attttgttag tacgattgat | 6720 |
| ttacctaatt | atggatgcac | aattcctgaa | aagaccagtt | gcagtgttta tggctggggc | 6780 |
| tacactggat | tgatcaacta | tgatggccta | ttacgagtgg | cacatctcta tataatggga | 6840 |
| aatgagaaat | gcagccagca | tcatcgaggg | aaggtgactc | tgaatgagtc tgaaatatgt | 6900 |
| gctggggctg | aaaagattgg | atcaggacca | tgtgaggggg | attatggtgg cccacttgtt | 6960 |
| tgtgagcaac | ataaaatgag | aatggttctt | ggtgtcattg | ttcctggtcg tggatgtgcc | 7020 |
| attccaaatc | gtcctggtat | ttttgtccga | gtagcatatt | atgcaaaatg gatacacaaa | 7080 |
| attattttaa | catataaggt | accacagtca | tag | | 7113 |

<210> SEQ ID NO 8
<211> LENGTH: 89
<212> TYPE: PRT
<213> ORGANISM: Homo sapiens

<400> SEQUENCE: 8

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 9
<211> LENGTH: 245
<212> TYPE: DNA
<213> ORGANISM: Artificial Sequence
<220> FEATURE:
<223> OTHER INFORMATION: Synthetic Construct

<400> SEQUENCE: 9

```
gtaagaacag tatgaagaaa agagatgaag cctctgtctt ttttacatgt taacagtctc    60
atattagtcc ttcagaataa ttctacaatc ctaaaataac ttagccaact tgctgaattg   120
tattacggca aggtttatat gaattcatga ctgatattta gcaaatgatt aattaatatg   180
ttaataaaat gtagccaaaa caatatctta ccttaatgcc tcaatttgta gatctcggta   240
tttgt                                                               245
```

<210> SEQ ID NO 10
<211> LENGTH: 307
<212> TYPE: DNA
<213> ORGANISM: Artificial Sequence
<220> FEATURE:
<223> OTHER INFORMATION: Synthetic Construct

<400> SEQUENCE: 10

```
ttatgtttca gacaacttcg attcagttct agaatgtttg actcagcaaa ttcacaggct    60
catctttcta acttgatggt gaatatggaa attcagctaa atggatgtta ataaaattca   120
aacgttttaa ggacagatga aaatgacaga atttttaaggt aaaatatatg aaggaatata   180
agataaagga tttttctacc ttcagcaaaa acatacccac taattagtaa aattaatagg   240
caaaaaaaag ttgcatgctc ttatactgta atgattatca ttttaaaact agcttttgc   300
cttcgag                                                             307
```

<210> SEQ ID NO 11
<211> LENGTH: 4941
<212> TYPE: DNA
<213> ORGANISM: Artificial Sequence
<220> FEATURE:
<223> OTHER INFORMATION: Synthetic Construct

<400> SEQUENCE: 11

```
gtaagaacag tatgaagaaa agagatgaag cctctgtctt ttttacatgt taacagtctc    60
atattagtcc ttcagaataa ttctacaatc ctaaaataac ttagccaact tgctgaattg   120
tattacggca aggtttatat gaattcatga ctgatattta gcaaatgatt aattaatatg   180
ttaataaaat gtagccaaaa caatatctta ccttaatgcc tcaatttgta gatctcggta   240
tttgtgaaat aataacgtaa acttcgttta aaaggattct tcttcctgtc tttgagaaag   300
tacggcactg tgcaggggga gaggttgatt gtgaaaaatc agaggtagat gagaatctta   360
ctgagggctg agggttcttt aaccttggtg gatctcaaca ttggttgcac attaaaatca   420
cctgctgcaa gcccttgacg aatcttactt agaagatgac aacacagaac aattaaatca   480
gaatctctgg ggagaatagg gcaccagtat ttttttgagct cccaccatga ttccaaagtg   540
cagccaaatt tgagaaccac tgctaaaagc tcaagcttca gattgaccag cttttccatc   600
tcacctatcg cctaaagacc aaattggata aatgtgttca ttacgacaga tgggtactat   660
ttaaagatga gtaaacacaa tatacttagg ctcgtcagac tgagagtttt aatcatcact   720
gaggaaaaac atagatatct aatactgact ggagtattag tcaaggctta tttcacacac   780
```

```
aattttatca gaaaccaaag tagtttaaaa cagctctccc cttattagta atgcattgga    840
gggtttactt taccatgtac cttgctgagc actgtacctt gttaatctca tttacttgta    900
atgagaacca cacagcgggt agttttattg gttctatttt acctacatga caaaactgaa    960
gcataaaaac acttagtaag ttttcagtgt catgcacaac taggaagtga catggccaga   1020
atataagccc agtcaccatc actctataac ctgcgctttt aacaacttca gggcatgaca   1080
catttggccg gtcagtagaa cccatgctgt gatttgtttt tgcagtggtg gtgatgactg   1140
ccttgttgaa tccactttt attctattcc attttgggga cacaattctg caagatgatt    1200
cttcattagg aaacagagat gagttattga ccaacacaga aagaaaaga gtttgttgct    1260
ccacactggg attaaaccta tgatcttggc ctaattaaca ctagctagta agtgtccaag   1320
ctgatcatct ctacaacatt tcaataacag aaaacaacaa ttttcaaaat tagttactta   1380
caattatgta gaaatgcctc taaaacacag tattttcctt atattacaaa aacaaaaatt   1440
ataattggtt ttgtcctctt ttgagagttt gcatggtgtt actccctgca tagtgaagaa   1500
aacattttat ttaagtagat ggatctaagt ttttcatgaa caaaggaatg acatttgaaa   1560
tcaatcctac cctagtccag gagaatgcat tagattaacc tagtagaggt cttatttcac   1620
cctgagtttt ctatgatcgt gattctctgc tggaggagta attgtgaaat agatctctct   1680
gggaactggc ttcctagtcc aatcagctct tttaccaatg aacacttcct tgtgatatag   1740
atgtttatgg ccgagaggat ccagtatatt aataaaatcc cttttgtat tcaatgaggg    1800
aaacacataa ttttcatcaa ttagcagctt attggaatat ctgcatgatg gtttaacact   1860
tttaagtgtt gactaaagat taattttaca gaaaatagaa aaagaaatat gtttctgtct   1920
ggaggaatga tttattgttg acccctaaat tgaaatattt tactagtggc ttaatggaaa   1980
gatgatgaaa gatgatgaaa ttaatgtaga agcttaacta gaaaatcagg tgacctgata   2040
tctacatctg tatccttcat tggccaccca gcattcatta atgaatcaga tgatggaata   2100
gatcaagttt cctaggaaca cagtgaatat taaaagaaaa caagggagc ctagcaccta    2160
gaagacctag tttatatttc aaagtatatt tggatgtaac ccaatttaa acatttcctc    2220
acttgtctct cttaaagcct tgccaacagc aaggacagag aaccaaaat agtgtatata    2280
tgaataaatg cttattacag aatctgctga ctggcacatg ctttgtgtgt aatgggttct   2340
cataaacact tgttgaatga acacacataa gtgaaagagc atggctaggc ttcatcccc    2400
ggtcaaatat ggggtgctaa agaaaagcag gggaaataca ttgggacact aacaaaaaaa   2460
aacagttaat ttaggtaaaa gataaaatac accacagaat gaagaaaaga gatgacccag   2520
actgctcttt aaccttcatg tcctagagag gttttttgata tgaattgcat tcagaattgt   2580
ggaaaggagc ccatctttc tcttcatttt gatttttatta actccaatgg gggaatttta   2640
ttcgtgtttt ggccatatct acttttgatt tctacattat tctctcttcc tttctacctg   2700
tatttgtcct aataaattgt tgacttatta attcactact tcctcacagc ttttttttgg   2760
ctttacaaat ccactggaaa ggtatatggg tgtatcactt tgtgtatttc ggtgtgcatg   2820
tgtagagggg acaaaaatcc tctctcaaac tataaatatt gagtatttgt gtattgaaca   2880
tttgctataa ctactaggtt tcttaaataa tcttaatata taaatgata tagaaaaagg    2940
gaaattatag ttcgtattat tcatctaagt gaagagatta aaacccaggg agtaaataaa   3000
ttgtctaagg actaaggttg tatactattt aggtgataga tatggggcaa ccgtatgggt   3060
tttatgatta acaaataaac ttctcaccac tctaccatat caacttttcc ataaaagaga   3120
gctatagtat tctttgctta aataaatttg attagtgcat gacttcttga aaacatataa   3180
```

-continued

```
agcaaaagtc acatttgatt ctatcagaaa agtgagtaag ccatggccca aacaaaagat    3240
gcattaaaat attctggaat gatggagcta aaagtaagaa aaatgacttt ttaaaaaagt    3300
ttactgttag gaattgtgaa attatgctga attttagttg cattataatt tttgtcagtc    3360
atacggtctg acaacctgtc ttatttctat ttccccatat gaggaatgct agttaagtat    3420
ggatattaac tattactact tagatgcatt gaagttgcat aatatggata atacttcact    3480
ggttccctga aaatgtttag ttagtaataa gtctcttaca ctatttgttt tgtccaataa    3540
tttatatttt ctgaagactt aactctagaa tacactcatg tcaaaatgaa agaatttcat    3600
tgcaaaatat tgcttggtac atgacgcata cctgtatttg ttttgtgtca caacatgaaa    3660
aatgatggtt tattagaagt ttcattgggt aggaaacaca tttgaatggt atttactaag    3720
atactaaaat ccttggactt cactctaatt ttagtgccat ttagaactca aggtctcagt    3780
aaaagtagaa ataaagcctg ttaacaaaac acaagctgaa tattaaaaat gtaactggat    3840
tttcaaagaa atgtttactg gtattacctg tagatgtata ttctttatta tgatcttttg    3900
tgtaaagtct ggcagacaaa tgcaatatct aattgttgag tccaatatca caagcagtac    3960
aaaagtataa aaaagacttg gccttttcta atgtgttaaa atactttatg ctggtaataa    4020
cactaagagt agggcactag aaattttaag tgaagataat gtgttgcagt tactgcactc    4080
aatggcttac tattataaac caaaactggg atcactaagc tccagtcagt caaaatgatc    4140
aaaattattg aagagaataa gcaattctgt tctttattag gacacagtag atacagacta    4200
caaagtggag tgtgcttaat aagaggtagc atttgttaag tgtcaattac tctattatcc    4260
cttggagctt ctcaaaataa ccatataagg tgtaagatgt taaaggttat ggttacactc    4320
agtgcacagg taagctaata ggctgagaga agctaaatta cttactgggg tctcacagta    4380
agaaagtgag ctgaagtttc agcccagatt taactggatt ctgggctctt tattcatgtt    4440
acttcatgaa tctgtttctc aattgtgcag aaaaaagggg gctatttata agaaaagcaa    4500
taaacaaaca agtaatgatc tcaaataagt aatgcaagaa atagtgagat ttcaaaatca    4560
gtggcagcga tttctcagtt ctgtcctaag tggccttgct caatcacctg ctatcttta    4620 gtggagcttt gaaattatgt ttcagacaac ttcgattcag ttctagaatg tttgactcag    4680
caaattcaca ggctcatctt tctaacttga tggtgaatat ggaaattcag ctaaatggat    4740
gttaataaaa ttcaaacgtt ttaaggacag atgaaaatga cagaatttta aggtaaaata    4800
tatgaaggaa tataagataa aggattttc taccttcagc aaaaacatac ccactaatta    4860
gtaaaattaa taggcaaaaa aaagttgcat gctcttatac tgtaatgatt atcattttaa    4920
aactagcttt ttgccttcga g                                              4941
```

METHOD FOR TREATING PERIPHERAL VASCULAR DISEASE USING HEPATOCYTE GROWTH FACTOR AND STROMAL CELL DERIVED FACTOR 1A

SEQUENCE LISTING

The instant application contains a Sequence Listing which has been submitted electronically in ASCII format and is hereby incorporated by reference in its entirety. Said ASCII copy, created on Dec. 24, 2019 is named 50413_199001_Sequence_Listing_122419_ST25 and is 42,887 bytes in size.

TECHNICAL FIELD

The present invention relates to a composition for preventing or treating a peripheral artery disease, the composition comprising: as active ingredients, hepatocyte growth factor (HGF) or an isoform thereof, and stromal cell derived factor 1α (SDF-1α); or polynucleotides encoding the proteins.

BACKGROUND ART

This application claims priority to and the benefit of Korean Patent Application No. 10-2014-0129361 filed in the Korean Intellectual Property Office on Sep. 26, 2014, the disclosure of which is incorporated herein by reference. Cardiovascular diseases are caused by the narrowing or occlusion of blood vessels due to atherosclerosis or the like. Cardiovascular diseases are largely divided into coronary artery disease (CAD) and peripheral artery disease (PAD). Among these, ischemic limb disease is a representative type of peripheral artery diseases.

Until now, the use of drugs to expand blood vessels or surgical operations account for the majority of the treatment of cardiovascular diseases. However, in the case of an ischemic limb disease, the pain caused by the body decay is so severe that some patients take an antipsychotic painkiller and, if the body decay gets worse, the legs of the patients are amputated or the patients die. Therefore, fundamental treatment therefor is needed.

Meanwhile, expression vectors as gene delivery systems for gene therapy are disclosed in WO 2000/040737. In addition, WO 2003/078568 discloses the therapeutic effects for ischemic hindlimb disease using HGF gene.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors researched and endeavored to develop drugs capable of preventing or treating a peripheral artery disease. As a result, the present inventors verified that the use of: hepatocyte growth factor (HGF) or an isoform thereof, and stromal cell derived factor 1α (SDF-1α); or polynucleotides encoding the proteins, in combination, had a remarkable therapeutic effect on a peripheral artery disease than the use of HGF, SDF-1α, or polynucleotides encoding the proteins thereof alone, and thus completed the present invention.

Therefore, an aspect of the present invention is to provide a pharmaceutical composition for preventing or treating a peripheral artery disease.

Another aspect of the present invention is to provide a method for preventing or treating a peripheral artery disease.

Other purposes and advantages of the present invention will become more obvious with the following detailed description of the invention, claims, and drawings.

Technical Solution

In accordance with an aspect of the present invention, there is provided a pharmaceutical composition for preventing or treating a peripheral artery disease (PAD), the pharmaceutical composition containing: as active ingredients, (a) hepatocyte growth factor (HGF) or an isoform thereof, and stromal cell derived factor 1α (SDF-1α); or (b) a polynucleotide encoding HGF and a polynucleotide encoding SDF-1α.

The present inventors researched and endeavored to develop drugs capable of preventing or treating a peripheral artery disease. As a result, the present inventors verified that the use of: hepatocyte growth factor (HGF) or an isoform thereof, and stromal cell derived factor 1α (SDF-1α); or polynucleotides encoding the proteins, in combination, had a remarkable therapeutic effect on a peripheral artery disease than the use of HGF, SDF-1α, or polynucleotides encoding the proteins thereof alone.

The therapy strategy of the present invention may be largely classified into two types: protein therapy and gene therapy. According to the protein therapeutic agent strategy of the present invention, HGF protein or an isoform thereof and SDF-1α protein are used in combination. Meanwhile, according to the gene therapeutic agent strategy of the present invention, at least one nucleotide sequence encoding HGF and at least one nucleotide sequence encoding SDF-1α are administered. At least one nucleotide sequence encoding HGF and at least one nucleotide sequence encoding SDF-1α may be provided as one polynucleotide or separate polynucleotides. According to one embodiment of the present invention, at least one nucleotide sequence encoding HGF and at least one nucleotide sequence encoding SDF-1α are provided as separate polynucleotides.

Hereinafter, the present invention will be described in detail.

As used herein, the term "isoform of HGF" refers to an HGF polypeptide having an amino acid sequence that is at least 80% identical to a naturally occurring HGF amino acid sequence in an animal, including all allelic variants. For example, the term "isoform of HGF" has a meaning that includes all of a normal form or a wild type of HGF and various variants of HGF (e.g., splicing variants and deletion variants).

As used herein, the term "prevention" refers to all the acts of suppressing a peripheral artery disease or delaying the progress of a peripheral artery disease through the administration of the composition of the present invention.

As used herein, the term "treatment" refers to (a) suppression of the development of a peripheral artery disease; (b) alleviation of a peripheral artery disease; and (c) removal of a peripheral artery disease.

According to an embodiment of the present invention, the HGF of the present invention includes a recombinant human HGF protein. According to another embodiment of the present invention, the HGF includes the amino acid sequence of SEQ ID NO: 1.

According to an embodiment of the present invention, the isoform of the HGF includes full-length HGF (flHGF) and deleted variant HGF (dHGF).

As used herein, the term "flHGF" refers to a sequence of amino acids 1-728 of animal HGF; a sequence of amino acids 1-728 of mammalian HGF for an embodiment; and a sequence of amino acids 1-728 of human HGF for another embodiment.

As used herein, the term "dHGF" refers to a deleted variant of the HGF protein produced by alternative splicing of the animal HGF gene; and the mammal HGF gene for an embodiment. According to another embodiment of the present invention, the dHGF of the present invention refers to human HGF composed of 723 amino acids with the deletion of five amino acids (F, L, P, S, and S) in the first kringle domain of the alpha chain from the full-length HGF sequence.

According to an embodiment of the present invention, the full-length HGF of the present invention includes the amino acid sequence of SEQ ID NO: 2, and the deleted variant HGF of the present invention includes the amino acid sequence of SEQ ID NO: 3.

According to an embodiment of the present invention, SDF-1α of the present invention includes the amino acid sequence of SEQ ID NO: 4 or SEQ ID NO: 8.

As validated in the following examples, the co-treatment of HUVEC with the HGF and SDF-1α proteins of the present invention promoted the degrees of migration and angiogenesis of the vascular endothelial cells more effectively compared with the treatment with the proteins alone, and thus, it was verified that the co-administration of HGF and SDF-1α proteins can be effectively used for the prevention or treatment of a peripheral artery disease.

According to an embodiment of the present invention, an isoform of HGF of the present invention is encoded by separate nucleotide sequences or a single polynucleotide sequence. Herein, the pharmaceutical composition of the present invention includes two or more polynucleotides when an isoform of HGF is encoded by separate polynucleotides, and includes at least one polynucleotide including a single polynucleotide when an isoform of HGF is encoded by the single polynucleotide. The polynucleotides of the present invention may be operatively linked to at least one regulatory sequence (e.g., a promoter or an enhancer) regulating the expression of an isoform of HGF.

When the isoforms of HGF are encoded by separate polynucleotides, an expression cassette may be constructed in two manners. According to a first manner, the expression cassette is constructed by linking an expression regulatory sequence to a coding sequence (CDS) of each isoform. According to a second manner, the expression cassette is constructed by using an internal ribosomal entry site (IRES), like "expression regulatory sequence—first isoform CDS—IRES—second isoform CDS—transcription termination sequence", or peptide 2A sequence, in the same manner as "expression regulatory sequence—first isoform CDS—IRES—second isoform CDS—transcription termination sequence". The IRES allows two or more genes of interest to be expressed in the same construct by starting the gene translation at the IRES sequence.

When an isoform of HGF is encoded by a single polynucleotide, the polynucleotide encoding all the isoforms is operatively linked to a single expression regulatory sequence.

In the present invention, an isoform of HGF may be encoded by a hybrid HGF gene that simultaneously expresses two or more different kinds of isoforms, for example, flHGF and dHGF.

According to an embodiment of the present invention, the hybrid HGF gene includes the sequence corresponding to exons 1 to 4 of human HGF gene, intron 4 of human HGF gene or a fragment sequence thereof, and a sequence corresponding to exons 5 to 18 of human HGF gene.

The hybrid HGF gene including intron 4 is 7113-bp long and includes the nucleotide sequence of SEQ ID NO: 7. The hybrid HGF gene may selectively include a fragment of intron 4 between exon 4 and exon 5 of HGF cDNA. According to a particular embodiment of the present invention, the hybrid HGF gene includes the nucleotide sequence of SEQ ID NO: 5.

The "isoform of HGF" of the present invention and hybrid HGF gene (e.g., HGF-X7) have been reported in WO 2003/078568, the disclosure of which is incorporated herein by reference.

The amino acid or nucleotide sequence of an isoform of HGF usable in the present invention is construed to include an amino acid or nucleotide sequence that is substantially identical to an isoform of wild type human HGF. The term "substantial identity" means that, when the amino acid or nucleotide sequence of an isoform of wild type human HGF and any different nucleotide sequence are aligned to correspond to each other as much as possible and the aligned sequences are analyzed using an algorithm that is ordinarily used in the art, the amino acid or nucleotide sequence of an isoform of wild type human HGF shows at least 80% identity, preferably at least 90% identity, and most preferably at least 95% identity. Methods of alignment for sequence comparison are known in the art. Various methods and algorithms for alignment are disclosed in Smith and Waterman, Adv. Appl. Math. 2:482 (1981); Needleman and Wunsch, J. Mol. Bio. 48:443 (1970); Pearson and Lipman, Methods in Mol. Biol. 24: 307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. BioSci. 8:155-65 (1992), and Pearson et al., Meth. Mol. Biol. 24:307-31 (1994). The NCBI Basic Local Alignment Search Tool (BLAST) (Altschul et al., J. Mol. Biol. 215:403-10 (1990)) is available via the National Center for Biological Information (NBCI) or the like, and on the Internet, may be used in connection with the sequence analysis programs, such as blastp, blasm, blastx, tblastn, and tblastx. BLAST can be accessed through www.ncbi.nlm.nih.gov/BLAST/. The sequence identity comparison method using such a program can be confirmed in www.ncbi.nlm.nih.gov/BLAST/blast_help.html.

According to an embodiment of the present invention, the polynucleotide encoding SDF-1α of the present invention includes SEQ ID NO: 6.

According to an embodiment of the present invention, the peripheral artery disease of the present invention is an ischemic limb disease. As validated in the following examples, the composition of the present invention has an effect of maintaining a normal state continuously, unlike the pCK administration group, pCK-SDF-1α administration group, and pCK-HGF administration, showing degradations in hindlimb conditions in hindlimb ischemia-induced mouse models.

According to an embodiment of the present invention, each of the polynucleotides of the present invention is naked DNA or a nucleotide contained in a gene delivery system.

The composition of the present invention may be applied in vivo through a variety of delivery methods that are routinely known in a field of gene therapy, and the gene delivery system includes, but is not limited to, for example, a vector, a plasmid, and a viral vector.

(i) Plasmid (Vector)

A plasmid (vector) may be used as a delivery system that delivers the polynucleotides of the present invention. The polynucleotide included in the vector is preferably present in a suitable expression cassette. In the expression cassette, the polynucleotide is, preferably, operatively linked to a promoter.

As used herein, the term "operatively linked" refers to a functional linkage between a nucleic acid expression regulatory sequence (e.g., a promoter, a signal sequence, or an array of transcription regulation factor binding sites) and another nucleic acid sequence, and through the linkage, the regulatory sequence regulates the transcription and/or translation of the another nucleic acid sequence.

In the present invention, the promoter linked to the polynucleotide sequence is one that can regulate the transcription of the nucleotide sequence by operating in animal cells according to an embodiment, mammalian cells according to another embodiment, and human cells according to a particular embodiment, and includes promoters derived from mammalian viruses and promoters derived from mammalian cell genomes. Examples thereof may include cytomegalovirus (CMV) promoter, adenovirus late promoter, vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter, but are not limited thereto. According to an embodiment of the present invention, the promoter used in the present invention is a promoter or EF1 alpha promoter derived from the human CMV (hCMV) immediately early (IE) gene. According to another embodiment, the promoter used in the present invention is a 5' untranslated region (UTR) including a promoter/enhancer and the sequence from the entire nucleotides of exon 1 to the nucleotide immediately before ATG initiation codon of exon 2, in the CMV IE gene.

The expression cassette used in the present invention may include a polyadenylation sequence, and may include, for example, a bovine growth hormone terminator (Gimmi, E. R., et al., Nucleic Acids Res. 17:6983-6998 (1989)), SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. Biol. 5:2104-2113 (1985)), or polyoma virus polyA (Batt, D. B and G. G. Carmichael, Mol. Cell. Biol. 15:4783-4790 (1995)), but is not limited thereto.

According to another embodiment of the present invention, pCK, pCP, pVAX1, or pCY vector may be used as a gene delivery system of the present invention, and according to a particular embodiment of the present invention, pCK vector may be used. The pCK vector is disclosed in detail in WO 2000/040737, the disclosure of which is incorporated herein by reference.

(ii) Retrovirus

Retroviruses can introduce a gene thereof into the genome of a host to deliver a lot of exotic genetic materials, and have a wide spectrum of infectible cells, and thus most retroviruses are used as gene delivery vectors.

In order to construct a retrovirus vector, the polynucleotide sequence of the present invention is inserted into the retroviral genome instead of the retroviral sequence, thereby producing replication-deficient viruses. For virion production, a packaging cell line comprising gag, pol, and env genes but not long terminal repeat (LTR) sequence and ψ sequence is constructed (Mann et al., Cell, 33:153-159 (1983)). When the recombinant plasmid including the polynucleotide sequence of the present invention, the LTR sequence, and the ψ sequence, is inserted into the cell line, the ψ sequence allows the production of RNA transcripts of the recombinant plasmid, and these transcripts are packaged with viruses, which are then discharged to a medium (Nicolas and Rubinstein "Retroviral vectors," In: Vectors: A survey of molecular cloning vectors and their uses, Rodriguez and Denhardt (eds.), Stoneham: Butterworth, 494-513 (1988)). The medium containing the recombinant retroviruses is collected and concentrated, and then used as a gene delivery system.

Gene delivery using a second-generation retroviral vector has been published. Kasahara et al., manufactured a moloney murine leukemia virus variant, and produced a chimeric protein having new binding characteristics by inserting the erythropoietin (EPO) sequence into an envelope site of the variant (Science, 266:1373-1376 (1994)). The polynucleotide sequence of the present invention may also be loaded in the retrovirus according to the construction strategy of such a second-generation retroviral vector.

(iii) Adenovirus

Adenovirus has usually been employed as a gene delivery vector due to the mid-sized genome, ease of engineering, a high titer, wide range of target cells, and high infectivity. Both ends of the genome contain 100-200 bp inverted terminal repeats (ITRs), which are cis-elements necessary for DNA replication and packaging. E1 region (E1A and E1B) of the genome encodes proteins responsible for the regulation of transcription of the viral genome and the transcription of host cell genes. E2 regions (E2A and E2B) encode the proteins involved in viral DNA replication.

Of adenoviral vectors developed so far, a replication-deficient adenovirus having a deleted E1 region is usually used. Meanwhile, an E3 region is removed from a normal adenoviral vector to provide an insertion site for an exotic gene (Thimmappaya, B. et al., Cell, 31:543-551 (1982); Riordan, J. R. et al., Science, 245:1066-1073 (1989)). Therefore, the polynucleotide sequence of the present invention is preferably inserted into either a deleted E1 region (E1A region and/or E1B region) or a deleted E3 region. In addition, the polynucleotide sequence may also be inserted into a deleted E4 region. Herein, the term "deletion" used with reference to viral genome sequences encompasses the complete deletion of the corresponding sequence as well as the partial deletion thereof. In addition, the adenovirus can package approximately 105% of the wild-type genome, and thus, can package about 2 extra kb of DNA (Ghosh-Choudhury et al., EMBO J., 6:1733-1739 (1987)). Therefore, the foregoing exotic sequences inserted into adenovirus may be further inserted into the adenoviral genome.

Adenovirus may be of any one of 42 different serotypes and subgroups A-F. Of these, adenovirus type 5 pertaining to subgroup C is the most preferable starting material for obtaining the adenoviral vector of the present invention. Biochemical and genetic information about adenovirus type 5 has been well known. The exotic genes delivered by the adenovirus are replicated in the same manner as in the episome, and thus have low genotoxicity to host cells.

Therefore, gene therapy using the adenoviral gene delivery system is considered to be safe.

(iv) AAV Vector

Adeno-associated viruses (AAV) are capable of infecting non-divided cells and have the ability to infect various types of cells, and thus are suitable as a gene delivery system of this invention. Detailed descriptions for the use and preparation of the AAV vector are disclosed in U.S. Pat. Nos. 5,139,941 and 4,797,368.

Research results for AAV as a gene delivery system are disclosed in LaFace et al, Viology, 162:483486 (1988), Zhou et al., Exp. Hematol. (NY), 21:928-933 (1993), Walsh et al, J. Clin. Invest., 94:1440-1448 (1994), and Flotte et al., Gene Therapy, 2:29-37 (1995). Recently, the AAV vector has been approved for Phase I human trials for the treatment of cystic fibrosis.

Typically, the AAV virus is manufactured by co-transfecting a plasmid containing a target gene sequence flanked by two AAV terminal repeats (McLaughlin et al., J. Virol., 62:1963-1973 (1988); and Samulski et al., J. Virol., 63:3822-3828 (1989)) and an expression plasmid containing a wild type AAV coding sequence without terminal repeats (McCarty et al., J. Virol., 65:2936-2945 (1991)).

(v) Other Viral Vectors

Other viral vectors may also be used to deliver the polynucleotide sequence of the present invention into the body. Vectors derived from viruses, such as vaccinia virus (Puhlmann M. et al., Human Gene Therapy 10:649-657 (1999); Ridgeway, "Mammalian expression vectors," In: Vectors: A survey of molecular cloning vectors and their uses. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. Gene transfer. New York: Plenum Press, 117-148 (1986) and Coupar et al., Gene, 68:1-10 (1988)), lentivirus (Wang G. et al., J. Clin. Invest. 104(11):R55-62 (1999)), and herpes simplex virus (Chamber R., et al., Proc. Natl. Acad. Sci USA 92:1411-1415 (1995)) may be used in the present delivery systems for delivering the polynucleotides of the invention into cells.

(vi) Liposomes

Liposomes are formed spontaneously by phospholipids suspended in the aqueous medium. Liposome-mediated exotic DNA molecule delivery has been very successful as described in Sene, Biochim. Biophys. Acta, 721:185-190 (1982) and Nicolau et al., Methods Enzymol., 149:157-176 (1987). Liposomes entrapping the polynucleotide sequence of the present invention deliver the polynucleotide sequence into cells by interacting with cells through mechanism, such as endocytosis, adsorption onto cell surfaces, and fusion with plasma cellular membranes.

In cases where the polynucleotide sequence of the present invention is loaded in a naked recombinant DNA molecule or a plasmid (vector), the polynucleotide sequence may be introduced into cells by micro-injection (Capecchi, M. R., Cell, 22:479 (1980); and Harland & Weintraub, J. Cell Biol. 101:1094-1099 (1985)), phosphate calcium precipitation (Graham, F. L. et al., Virology, 52:456 (1973); and Chen & Okayama, Mol. Cell. Biol. 7:2745-2752 (1987)), electroporation (Neumann, E. et al., EMBO J., 1:841 (1982); and Tur-Kaspa et al., Mol. Cell Biol., 6:716-718 (1986)), liposome-mediated transfection (Wong, T. K. et al., Gene, 10:87 (1980); Nicolau and Sene, Biochim. Biophys. Acta, 721: 185-190 (1982); and Nicolau et al., Methods Enzymol., 149:157-176 (1987)), DEAE-dextran treatment (Gopal, Mol. Cell Biol., 5:1188-1190 (1985)), and gene bombardment (Yang et al., Proc. Natl. Acad. Sci., 87:9568-9572 (1990)).

When the polynucleotide sequence of the present invention is constructed based on the viral vector, the polynucleotide sequence may be delivered into cells by various viral infection methods known in the art. The infection of host cells using viral vectors are described in the above-mentioned cited documents.

According to another embodiment of the present invention, the gene delivery system is a vector.

According to a certain embodiment of the present invention, the vector is a plasmid. According to a particular embodiment of the present invention, the plasmid is pCK. The recombinant vectors including a single polynucleotide expressing two or more isoforms of HGF using the pCK vector are disclosed in detail in WO 2000/040737 and WO 2003/078568.

The composition of the present invention may contain a pharmaceutically acceptable carrier. The pharmaceutically acceptable carrier contained in the composition of the present invention is ordinarily used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

According to an embodiment of the present invention, the pharmaceutical composition of the present invention is parenterally administered. For example, the pharmaceutical composition of this invention may be administered by using, for example, intravenous administration, intraperitoneal administration, subcutaneous administration, intradermal administration, intraspinal administration, intrathecal administration, intraventricular administration, parenchymal administration, intracranial administration, intramuscular administration, or local administration. According to another embodiment of the present invention, the pharmaceutical composition of the present invention may be administered by using intramuscular administration, intraspinal administration, intrathecal administration, intraventricular administration, parenchymal administration, or intracranial administration.

The pharmaceutical composition of the present invention may be administered as an injection. The appropriate dose of the pharmaceutical composition of the present invention varies depending on factors, such as the formulating method, manner of administration, patient's age, body weight, gender, and severity of disease, time of administration, route of administration, excretion rate, and response sensitivity, and the ordinarily skilled practitioner can easily judge and prescribe the dose effective for the desired treatment or prevention.

According to an embodiment of the present invention, the HGF, an isoform thereof, and SDF-1α of the present invention are administered at a dose of 10 ng to 100 mg for each, and the polynucleotides encoding the proteins are administered at a dose of 1 µg to 100 mg for each. When the HGF, an isoform thereof, SDF-1α, or the polynucleotides encoding the same, are repeatedly administered once or more, the dose may be equal or different for each administration.

The pharmaceutical composition of the present invention is formulated using a pharmaceutically acceptable carrier and/or excipient, according to the method that is easily conducted by a person having ordinary skills in the art to which the present invention pertains, and the pharmaceutical composition may be prepared into a unit dosage form or may be inserted into a multidose container. Here, the dosage form may be a solution in an oily or aqueous medium, a suspension, an emulsion, an extract, a powder, a granule, a tablet, or a capsule, and may further contain a dispersant or a stabilizer.

In accordance with another aspect of the present invention, there is provided a method for preventing or treating a peripheral artery disease, the method including a step of administering a composition to a subject in need thereof, the composition containing, as active ingredients, (a) hepatocyte growth factor (HGF) or an isoform thereof, and stromal cell derived factor 1α (SDF-1α); or (b) a polynucleotide encoding HGF and a polynucleotide encoding SDF-1α.

As used herein, the term "administration" or "administer" refers to the direct application of a therapeutically effective amount of the composition of the present invention to a subject (i.e., an object) in need of the composition, thereby forming the same amount thereof in the body of the subject. Therefore, the term "administer" includes the injection of the composition of the present invention around a site of lesion, and thus the term is used in the same meaning as the term "inject".

The term "therapeutically effective amount" of the composition refers to the content of the composition, which is sufficient to provide a therapeutic or preventive effect to a subject to be administered, and thus the term has a meaning including "preventively effective amount". As used herein, the term "subject" includes, but is not limited to, human, mouse, rat, guinea pig, dog, cat, horse, cow, pig, monkey, chimpanzee, baboon, or rhesus monkey. Specifically, the subject of the present invention is human.

Since the method for preventing or treating peripheral artery disease of the present invention includes the step of administering the pharmaceutical composition for preventing or treating peripheral artery disease, which is an aspect of the present invention, the overlapping descriptions therebetween are omitted to avoid excessive complication of the specification.

Advantageous Effects

Features and advantages of the present invention are summarized as follows:

(a) The present invention provides a pharmaceutical composition for preventing or treating a peripheral artery disease (PAD).

(b) The use of the composition of the present invention can prevent or treat a peripheral artery disease (e.g., ischemic limb disease) more effectively through a remarkable promotion of the migration and angiogenesis of vascular endothelial cells when compared with the use of HGF, an isoform thereof, SDF-1α, or polynucleotides encoding the proteins alone.

BRIEF DESCRIPTION OF THE DRAWINGS

FIG. 3 illustrates an effect of the use of pCK-HGF and pCK-SDF-1α on the hindlimb conditions of hindlimb ischemia mouse models.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Experimental Method for Investigating Effect of Combination of HGF and SDF-1α on Cell Migration of Human Umbilical Vein Endothelial Cells (HUVECs)

HUVECs, which were obtained by taking only the endothelial cells of the vein from the human umbilical cord, making the cells into single cells, and culturing the single cells, were purchased from Lonza.

In order to investigate the effects of HGF (SEQ ID NO: 1, R&D systems Cat No. 294-HG-025/CF, USA) and SDF-1α (SEQ ID NO: 4, R&D systems Cat No. 350-NS-010/CF, USA) on the cell migration of HUVECs, the transwell (Corning, cat #3422) was coated with 1% gelatin, and then the cells were seeded at $2\times10^4$ cells per well. After the incubation for one hour to allow the cells to adhere, the experimental groups were organized as follows (50 ng/ml HGF; 50 ng/ml SDF-1α; 25 ng/ml HGF+25 ng/ml SDF-1α). The respective experimental groups were treated with corresponding proteins for 2 hours, and in order to measure the degree of cell migration, the cells were stained with crystal violet, and the number of migrated cells in the transwell was measured using a microscope.

Figure 1:
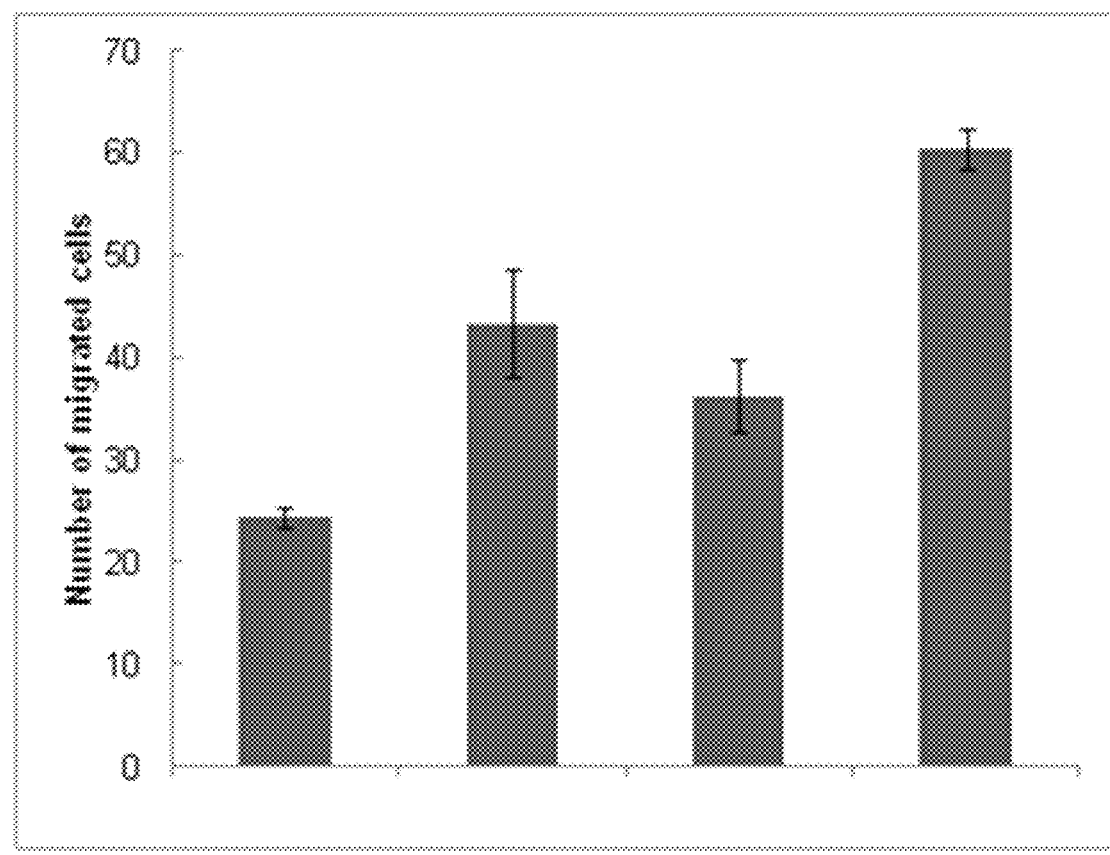
FIG. 1 illustrates an effect of the use of HGF and SDF-1α on the cell migration of HUVECs.

As a result, the treatment with 50 ng/ml HGF alone increased cell migration by 1.8-fold compared with the control, and the treatment with 50 ng/ml SDF-1α alone increased cell migration by 1.5-fold compared with the control. The co-treatment with HGF and SDF-1α at 25 ng/ml each increased cell migration by 2.5-fold compared with the control, showing a better effect on cell migration compared with the treatment with HGF and SDF-1α alone (FIG. 1).

Example 2: Investigation on Effect of Combination of HGF and SDF-1α on Angiogenesis in Matrigel Plug Assay The effect of HGF and SDF-1α on angiogenesis was investigated using Matrigel plug assay.

Five-week-old C57BL/6 mice were divided as follows to organize experimental groups (PBS; 300 ng HGF; 150 ng HGF+150 ng SDF-1α). Here, 1 unit of heparin was added to 400 µl Matrigel Matrix (Corning, cat #356231) and proteins corresponding to each experimental group were added. The resulting matrigel mixture was subcutaneously injected into the mouse abdomen. After 7 days, the mice were sacrificed and the transplanted matrigel matrix was isolated. In order to quantify the degree of angiogenesis, the level of hemoglobin contained in each matrigel was measured by Drabkin's assay.

Figure 2A:
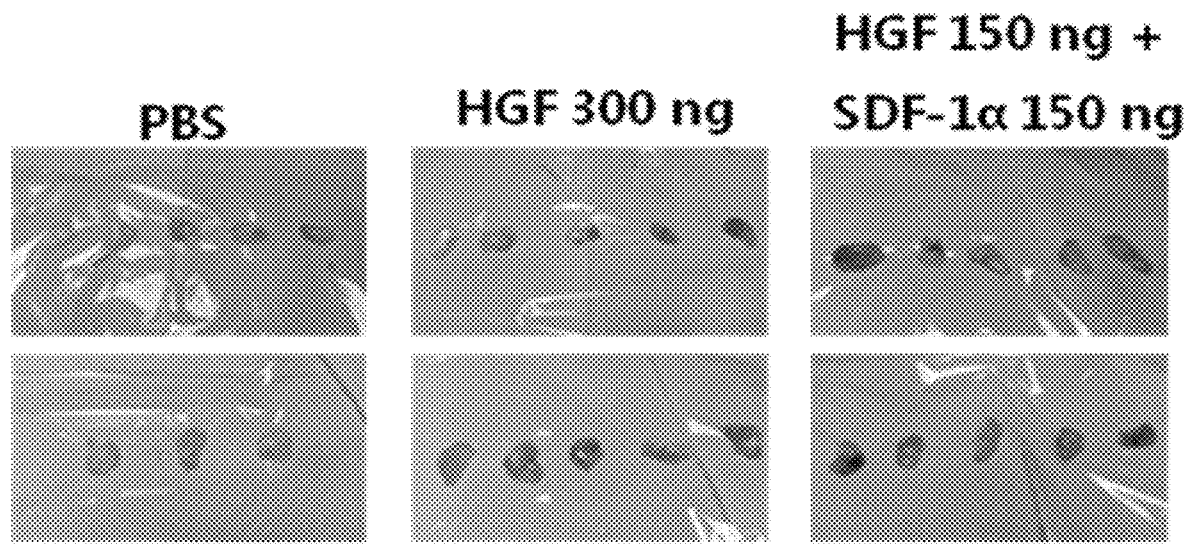
FIGS. 2a and 2b illustrate an effect of the use of HGF and SDF-1α on angiogenesis.
Figure 2B:
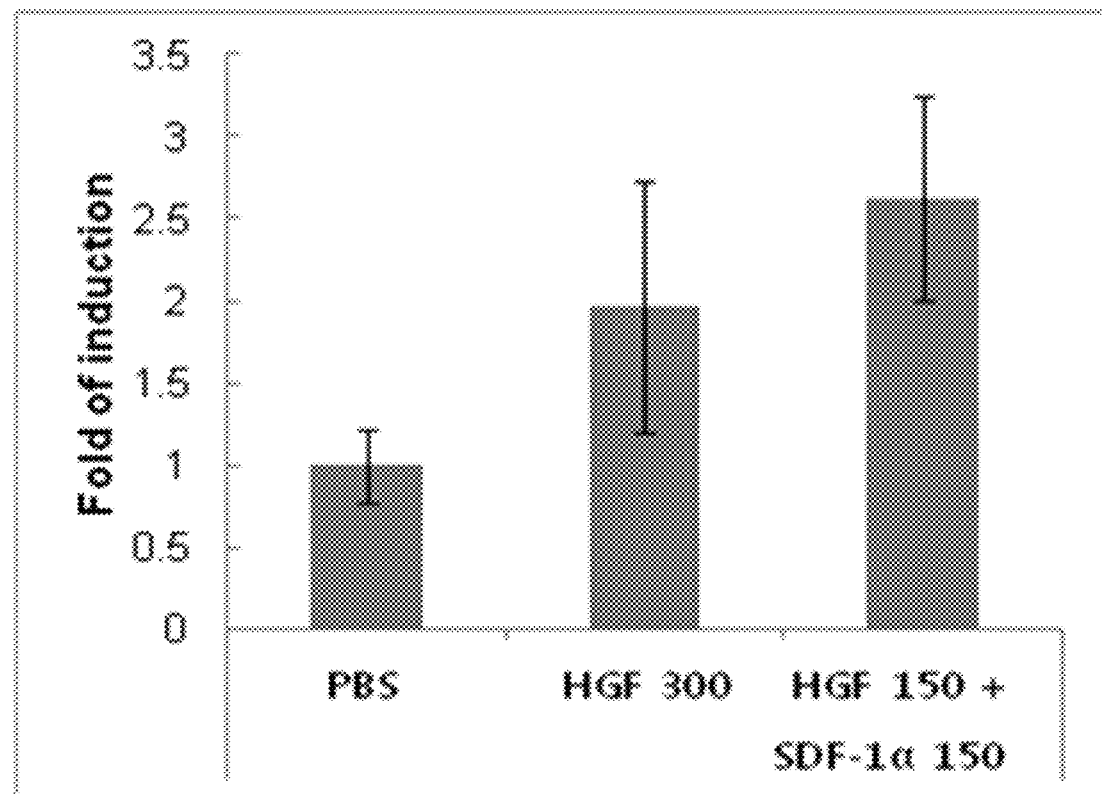

As a result, the group added with 300 ng HGF increased the level of hemoglobin by about 1.8-fold compared with the group added with PBS, and the group added with HGF and SDF-1α at 150 ng each increased the level of hemoglobin by about 2.3-fold compared with the group added with PBS, showing the improvement in the degree of angiogenesis compared with the administration with HGF alone (FIGS. 2a and 2b).

Example 3: Investigation on Effect of Administration with HGF and SDF-1α in Hindlimb Ischemia (HLI) Mouse Model Example 3-1: Preparation of Plasmid DNA Preparation of pCK-HGF Plasmid Prior to the experiment on the hindlimb ischemia mouse models, the plasmid DNA to be used was prepared in the following manner. The pCK vector is constructed such that a subject to be expressed is regulated under enhancer/promoter of the human cytomegalovirus (hCMV), and the pCK vector is disclosed in detail in Lee et al., Biochem. Biophys. Res. Commun. 272:230 (2000) and WO 2000/040737. The pCK-HGF plasmid used in the present invention was prepared by inserting, into the pCK vector, a hybrid gene (i.e., HGF-X7 gene; SEQ ID NO: 5) in which a fragment sequence of intron 4 of the human HGF gene is inserted between exons 4 and 5 of the human HGF gene according to the method disclosed in WO 2003/078568.

Preparation of pCK-SDF-1α

On the basis of the gene information of human SDF-1α (NCBI Reference Sequence: NM_199168.3), gene synthesis was conducted by adding the NheI and NotI restriction enzyme sequences to both ends of the gene. The synthesized human SDF-1α fragment was inserted into the pCK vector using NheI and NotI. The sequence of the human SDF-1α gene inserted into the pCK vector is the same as that of SEQ ID NO: 6.

Example 3-2: Preparation of Hindlimb Ischemia (HLI) Mouse Models and Administration of Plasmid DNA The HLI mouse model is the most representative mouse model to mimic human critical limb ischemia (CLI) [1, 2]. The method of producing the mouse model is as follows. Seven-week-old male Balb/c mice were anesthetized with a mixture of zoletil and rumpun, and the skin of the thigh was incised about 1 cm. After that, the position of the femoral artery inside the thigh was found to tightly bind a length of about 1 cm of the artery using 6-0 thickness of thread, and the tissue therebetween was cut out to remove the blood vessel. This method can induce ischemic conditions by removing blood vessels descending below the thigh. At the same time as the HLI induction, the plasmid DNA to be evaluated was administered to the muscle near the removed blood vessel. After that, the incision was sutured well and the mice were observed to recover from the anesthesia.

The HLI mouse models were organized into 6 mice per group, and each of the following plasmids was administered: 200 μg pCK; 200 μg pCK-HGF; 200 μg pCK-SDF-1α; 200 μg pCK-HGF+200 μg pCK-SDF-1α. At 3, 10, 17, 22, and 27 days after administration, the hindlimb conditions were observed, scored according to a predetermined criteria, and quantified. The criteria used here are as follows [3]: 0=normal state; 1=toenail necrosis; 2=toe necrosis; 3=foot tissue necrosis As a result, after the HLI induction, the group administered with pCK showed that the average hindlimb conditions began to deteriorate gradually, and the score after about two weeks increased to about 1.83. The group administered with pCK-HGF showed that the score increased to 0.66-0.83 over time. Meanwhile, the group co-administered with pCK-HGF and pCK-SDF-1α showed that the score after the HLI induction was maintained at zero (FIG. 3).

Resultantly, it was verified through examples 1-3 above that the effect of promoting the migration and angiogenesis of vascular endothelial cells and the treatment effect for an ischemic limb disease were more remarkable when HGF and SDF-1α were co-administered or the polynucleotides encoding HGF and SDF-1α respectively were co-administered rather than when the respective proteins or polynucleotides were administered alone.

REFERENCES

1. Limbourg, A., et al., Evaluation of postnatal arteriogenesis and angiogenesis in a mouse model of hindlimb ischemia. *Nat Protoc.* 4(12): p. 1737-46, 2009.
2. Couffinhal, T., et al., Mouse model of angiogenesis. *Am J Pathol.* 152(6): p. 1667-79, 1998.
3. Clayton, J. A., D. Chalothorn, and J. E. Faber, Vascular endothelial growth factor-A specifies formation of native collaterals and regulates collateral growth in ischemia. *Circ Res.* 103(9): p. 1027-36, 2008.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating a peripheral artery disease, the method comprising a step of local, intramuscular administration of a composition to a subject in need thereof, the composition comprising, a plasmid comprising a sequence encoding both full-length hepatocyte growth factor (flHGF) comprising the amino acid sequence of SEQ ID NO: 2 and deleted variant hepatocyte growth factor (dHGF) comprising the amino acid sequence of SEQ ID NO: 3, operably linked to a promoter, and a plasmid comprising a sequence encoding stromal cell derived factor 1α (SDF-1α) comprising the amino acid sequence of SEQ ID NO: 8, operably linked to a promoter, thereby treating a peripheral artery disease.

2. The method of claim 1, wherein the sequence encoding both the flHGF and the dHGF comprises the nucleotide sequence of SEQ ID NO: 5.

3. The method of claim 1, wherein the sequence encoding both the flHGF and the dHGF comprises the nucleotide sequence of SEQ ID NO: 7.

4. The method of claim 1, wherein the sequence encoding SDF-1α comprises the nucleotide sequence of SEQ ID NO: 6.

5. The method of claim 1, wherein the peripheral artery disease is ischemic limb disease.

6. The method of claim 1, wherein the plasmid is pCK.

7. The method of claim 1, wherein the subject is selected from the group consisting of human, mouse, rat, guinea pig, dog, cat, horse, cow, pig, monkey, chimpanzee, baboon, and rhesus monkey.

8. The method of claim 7, wherein the subject is human.

9. The method of claim 1, wherein the plasmids are administered at a dose of 1 µg to 100 mg for each.

* * * * *